(12) United States Patent
Wölfel

(10) Patent No.: US 9,138,348 B2
(45) Date of Patent: Sep. 22, 2015

(54) APPARATUS AND METHOD FOR OPERATING A LASER MATERIALS PROCESSING AND MEASUREMENT DEVICE

(75) Inventor: Mathias Wölfel, Erlangen (DE)

(73) Assignee: Wavelight Gmbh (DE)

( * ) Notice: Subject to any disclaimer, the term of this patent is extended or adjusted under 35 U.S.C. 154(b) by 481 days.

(21) Appl. No.: 12/965,243

(22) Filed: Dec. 10, 2010

(65) Prior Publication Data
US 2012/0145687 A1 Jun. 14, 2012

(51) Int. Cl.
*B23K 26/00* (2014.01)
*B23K 26/06* (2014.01)
*A61F 9/008* (2006.01)
*B23K 26/02* (2014.01)

(52) U.S. Cl.
CPC ............... *A61F 9/008* (2013.01); *B23K 26/02* (2013.01); *A61F 2009/00855* (2013.01)

(58) Field of Classification Search
CPC ...... A61F 9/008–9/0082; A61F 2009/008555; B23K 26/02–26/048
USPC ............. 219/121.6, 121.61, 121.73, 121.78, 219/121.82, 121.83; 606/4–6, 10–12, 17
See application file for complete search history.

(56) References Cited

U.S. PATENT DOCUMENTS 4,538,608 A * 9/1985 L'Esperance, Jr. ............... 606/3
5,049,147 A * 9/1991 Danon ........................... 606/10
6,139,542 A * 10/2000 Hohla ............................. 606/5
6,210,169 B1 * 4/2001 Yavitz ........................... 434/271
2002/0193704 A1 * 12/2002 Goldstein et al. ............. 600/558

OTHER PUBLICATIONS

Martin, R.C; "The Test Bus Imperative: Architectures That Support Automated Acceptance Testing", IEEE Software, Jul. 2005, 3 pages, 22:4, IEEE Computer Society Press Los Alamitos, CA, USA.
Abbot Medical Optics, Inc., "IntraLase Technology Truly Customizable Architecture", IntraLase FS and iFS Brochure, 2010, 12 pages, http://www.amo-ilasik.com/pdf/iFS%20Broch.pdf.
Alcon Laboratories, Inc., "Refractive Lenses | Diagnostics | Treatment Options", WaveLight Product Guide, International 2010.

* cited by examiner

*Primary Examiner* — Sang Y Paik

(57) ABSTRACT

An apparatus for operating a laser materials processing and measurement device with a controllable laser for generating a laser beam and beam control means for adjusting the focus zone of a controlled portion of the laser beam in three spatial directions comprises an interface for operating a bidirectional data transfer link with the laser and the beam control means, and user control means for inputting and displaying control commands or control command sequences and for monitoring and/or controlling operation and/or the operating state of the device. So that all the components of the apparatus may also be tested with regard to all functionalities, if the laser materials processing and measurement device is not operationally ready and/or not connected to the interface, according to the invention the apparatus comprises simulation means for simulating operation of the device and/or of the user control means.

17 Claims, 15 Drawing Sheets

| IN - SYS | OUT - SYS | |
|---|---|---|
| 1. Data in Scanner HIGH | | 1. |
| 2. | Scan enable HIGH | 2. |
|  Bed | | |
| 3. Energychange HIGH | | 3. |
| 4. | Scan enable LOW (Energychange) | 4. |
| 5. | Energy changed HIGH | 5. |
| 6. | Scan enable HIGH | 6. |
| 7. Energychange LOW | | 7. |
| 8. Sidecut | Energy changed LOW | 8. |
| 9. Data in Scanner LOW | | 9. |
| 10. | Scan enable LOW | 10. |

| Calibration | Scanchecks | Flap normal | Flap eliptical | Flap ring | Flap kerato | Scanfunctions | Service | Errorcodes | Limits | Values | System |

Error codes for scanning system

```
//*********************************************************
// Project      Scan DLL Module
// Copyright (c) 2007-2009
// Company      WaveLight AG
// File         ErrorCodes_00100100.h
// Version      00.10.01.00
// Author       Mathias Wolfel (mathias.woelfel@wavelight.com)
// Date         13.03.2009
// About        Error code definitions for RTCS.cpp and ScanDll.cpp
//---------------------------------------------------------
// History:
// 20.04.2007 - Creation of error list
// 18.08.2008 - Internal errors added
// 27.08.2008 - Internal errors added
// 22.09.2008 - Internal errors added
// V00.01.01.01
// V00.01.01.02
// 13.02.2009 - Internal errors added
// V00.01.01.03
// V00.01.01.04
// 09.03.2009 - Internal error set changed
// V00.02.00.00
// 13.03.2009 - Creation of error file
```

Fig. 14

| Calibration | Scanchecks | Flap normal | Flap eliptical | Flap ring | Flap kerato | Scanfunctions | Service | Errorcodes | Limits | Values | System |

System values (ATTENTION - don't change without knowledge!)

| Scale XY | 1650 | x and y scale factor [Bits/mm] | | Mark delay | 30 | mark delay [10*μs] |
| Scale Z | 1435 | z scale factor [Bits/mm] | | Jump delay | 30 | jump delay [10*μs] |
| Laser frequency | 200 | laser pulse frequency [kHz] | | Laser on delay | 100 | laser on delay [10*μs] |
| Goto speed | 7000 | speed for single jumps [Bits/ms] | | Laser off delay | 100 | laser off delay [10*μs] |
| Stretch speed | 20 | speed for z stretch jumps [Bits/ms] | | | | |
| Max. jump speed | 7000 | max speed for all jumps [Bits/ms] | | | | |
| Max. mark speed | 6600 | max speed for all marks [Bits/ms] | | | | |
| Check speed | 800 | mark speed for check pattern [Bit/ms] | | Copy all | | Apply new |
| Logo speed | 800 | mark speed for logo [Bits/ms] | | | | |

APPARATUS AND METHOD FOR OPERATING A LASER MATERIALS PROCESSING AND MEASUREMENT DEVICE

TECHNICAL FIELD

The present invention relates to an apparatus and a method for operating a laser materials processing and measurement device with a controllable laser for generating a laser beam and beam control means for adjusting the focus zone of a controlled portion of the laser beam in three spatial directions.

BACKGROUND

FIG. 1 shows a system for materials processing and for measuring by means of laser radiation comprising a laser materials processing and measurement device 10 and an apparatus 100' for controlling or operating the device 10. The device 10 comprises a controllable laser 14 for generating a laser beam 16, beam control means 18 for adjusting the focus zone of a controlled portion 20 of the laser beam in three spatial directions X, Y and Z, and an objective lens device 22 for collimating or focusing the controlled portion 20 of the laser beam 16 onto the material to be processed. The material to be processed may be a biological tissue, such as for instance a portion of an eye 12, in particular a human eye.

An apparatus 100' for controlling or operating the laser materials processing and measurement device 10 comprises a computer 102' with a display means 150 for displaying operating states of the laser materials processing and measurement device 10 and/or of the computer 102', input means 160 for inputting user commands for operating the computer 102' and user commands and/or command sequences for controlling or operating the device 10. The input means 160 may be a keyboard, a mouse, a light pen or also a touch-sensitive area (a touchscreen) which may be arranged over a screen of the display means 150. The apparatus 100' or computer 102' further comprises user control means 120 for inputting and displaying input control commands or control command sequences and for monitoring the operation or operating state of the device 10. In order to perform their functions, the user control means 120 are in operative connection with the display means 150 and the input means 160 via an internal bus system of the computer 102'.

The apparatus 100' or the computer 102' furthermore comprises control means 24 for driving the beam control means 18. The control means 24 may comprise a user-operable switch 162, for example a foot switch, for switching the laser materials processing and measurement device 10 on or off and/or for modifying the energy or intensity of the laser beam 16 generated by the laser 14. In order to perform the above-stated tasks, the control means 24 are connected with the beam control means 18 via a bidirectional data transfer link 190, 110, 180.

The apparatus 100' or computer 102' furthermore comprises a command library 140 for storing and providing beam control information or beam control commands for the beam control means 18 and optionally for the control means 24.

The apparatus 100' or the computer 102' furthermore comprises an interface 110 for transferring data or information between the command library 140 and the control means 24 and the controllable laser 14 or beam control means 18 of the device 10. The interface 110 is in operative connection via a first bidirectional data transfer link 180 with the controllable laser 14 and with the beam control means 18 and via a second bidirectional data transfer link 190 with the control means 24.

The user control means 120 may comprise hardware, such as for instance parts of a data memory of the computer 102', parts of a working memory of the computer 102', parts of a display surface of the display means 150, a drive for operating a data memory, control commands stored in the data and/or working memory of the computer 102' and user-specific software.

The command library 140 may comprise system-specific control commands and command sequences and software, such as for instance database software, for the laser materials processing and measurement device 10 stored in a data or working memory of the computer 102' for organising, managing and updating the control commands and control command sequences.

The control means 24 may comprise system-specific control electronics, control commands and status registers for the laser materials processing and measurement device 10 for storing and providing status information regarding the operation and/or the operating state of the device 10. The control means 24 may take the form of a plug-in card with the necessary electronics and the necessary memory means for plugging into a slot of the computer 102' or alternatively of a separate device with its own housing and its own interface 26.

The user control means 120 provide a user, for example a materials processing engineer, a doctor or an ophthalmic surgeon, with a user interface by means of which the user can operate, i.e. monitor and/or control, the operation and all the functions of the laser materials processing and measurement device 10. The user interface may comprise electromechanical operating and/or input elements, such as for instance switches, selector switches, rotary knobs, display devices, such as for instance alphanumeric displays, LCD displays, and/or also the above-stated input means 160 and display means 150 and software developed for system-specific driving of the display means and input means 160.

The apparatus 100' described with reference to FIG. 1 for operating the laser materials processing and measurement device 10 has a disadvantage, namely that testing of the device 10 or testing and/or updating of the apparatus 100' with the user control means 120, the command library 140, the control means 24 and/or the interface 110 may only be carried out if a completely assembled, operationally ready system comprising the laser materials processing and measurement device 10 and the apparatus 100' is available. Providing a complete system is not always practical. A first example of this is when only the user control means 120 and/or the user interface operated thereby are to be updated. In this case, an operative connection 180 between the apparatus 100' and the laser materials processing and measurement device 10 is unnecessary. A second example in which it is not practical to provide a complete system is when newly developed algorithms for operating the beam control means 18 are to be carried out, for example newly developed methods for materials processing and/or newly developed ophthalmic surgery methods, such as for instance algorithms for carrying out specific scans of the material to be processed or for carrying out laser-optical measurements on material arranged in the laser beam portion 20.

SUMMARY OF THE INVENTION

The present invention provides an apparatus and/or a method for operating a laser materials processing and measurement device, in which testing and/or updating of individual components, such as for instance the beam control means 18, the control means 24, the user control means 120 and/or the command library 140 may be carried out and tested, without, as described above, a complete system 10, 100' being available, and/or wherein only the particular components to be tested and/or updated and the other components of the system in operative connection with said components are available.

According to one aspect of the invention, an object of the invention is achieved by an apparatus for operating a laser materials processing and measurement device with a controllable laser for generating a laser beam and beam control means for adjusting the focus zone of a controlled portion of the laser beam in three spatial directions X, Y and Z. The apparatus comprises an interface for operating a first bidirectional data transfer link with the laser and the beam control means and user control means for inputting and displaying control commands or control command sequences and for monitoring and/or controlling the operation and/or the operating state of the laser materials processing and measurement device.

In accordance with the teachings of the invention, the apparatus furthermore can comprise simulation means for simulating the operation of the laser materials processing and measurement device and the user control means. Such simulation means make it possible to dispense with providing the laser materials processing and measurement device if only the user control means are to be updated and/or tested for complete functionality.

The simulation means may be configured to simulate operation of the laser materials processing and measurement device and/or of the user control means when the laser materials processing and measurement device is not operationally ready and/or not connected to the interface.

The various embodiments of the apparatus for operating the laser materials processing and measurement device of this invention may further comprise a display device for displaying input screens for control commands and/or control command sequences, and/or information relating to the operation and/or operating state of the laser materials processing and measurement device, and input means for inputting control commands and/or control command sequences and/or information relating to the operation and/or operating state of the laser materials processing and measurement device.

Such display and/or input means allow the operative interaction between the operating or control apparatus according to the invention and a user to be configured in a user-friendly manner.

The embodiments of the apparatus of the present invention may further comprise a command library for providing control commands and/or control command sequences to the interface. Such a command library makes it possible to provide all system-specific control commands and/or control command sequences for operation of the laser and/or of the beam control means centrally and/or in a compact memory area of a computer.

The simulation means furthermore can comprise testing means for simulating data transfer functions of the beam control means and/or of the laser materials processing and testing device. Such testing means make it possible to simulate operation and complete data transfer for controlling and monitoring the operation or operating state of the laser materials processing and measurement device via the interface, without the laser materials processing and measurement device itself being provided and/or operationally ready.

The control device may further comprise control means for driving the beam control means, wherein the interface is configured for operating a second bidirectional data transfer link with the control means and wherein the testing means are configured for simulating data transfer functions of the control means.

The control means may also comprise a user switch for switching the beam control means on or off, and the testing means comprise one or more of the following elements: simulation means for system-specific input means, such as for instance the user switch, simulation means for an energy change of the laser beam, display means for a loading status of a beam control command sequence and display means for a beam control output information. The display means for loading status may here in particular display information of the type "beam control command sequence loaded". The display means for beam control output information may in particular display information of the type "energy change necessary". Thanks to this configuration, the apparatus or computer, the user control means, the command library and/or the control means may be tested or updated, specifically with regard to all conceivable control commands and control command sequences for the laser materials processing and measurement device, even if neither the laser materials processing and measurement device nor the user switch is provided or in operationally ready operative connection with the apparatus or the computer.

The simulation means may be configured to simulate one or more of the following functions of the operation of the laser materials processing and measurement device:

setting and/or verifying basic settings of the laser materials processing and measurement device, predetermined types of calibration for the laser materials processing and measurement device, predetermined beam control tests for the beam control means of the laser materials processing and measurement device, predetermined materials processing operations, in particular predetermined surgical operations, which may be performed by the laser materials processing and measurement device, predetermined beam deflection functions, which may be performed by the beam control means, predetermined service functions of the laser materials processing and measurement device, outputting of error codes by the laser materials processing and measurement device, for example from an error file of the laser materials processing and measurement device, monitoring and/or complying with predetermined limit values for operating parameters of the laser materials processing and measurement device, for example by means of a limit value file of the laser materials processing and measurement device, in- and/or outputting of predetermined system operating parameters with regard to operation of the laser materials processing and measurement device, for example using an operating parameter register of the laser materials processing and measurement device, and outputting of system status parameters of the laser materials processing and measurement device, for example from a status parameter register of the laser materials processing and measurement device.

Such a configuration of the simulation means and of the laser materials processing and measurement device makes it possible for the laser materials processing and measurement device to be a device for carrying out predetermined ophthalmological surgical operations and for carrying out measurements on biological tissue, in particular on a human eye, with all currently conceivable ophthalmological operations.

For example, the predetermined beam control tests and/or the predetermined beam deflection functions may comprise a beam control test for an ophthalmological bed cut and a beam control test for an ophthalmological side cut.

The predetermined ophthalmological surgical operations may comprise a normal flap cut, an elliptical flap cut, a ring cut and/or a keratoplasty.

The predetermined beam deflection function may comprise a "Z-stretch" function and/or an "inclined plane".

The predetermined service functions may comprise a function for carrying out or cutting a test circle and/or a function for setting a series of randomly selected axial position changes (i.e. variable in the Z direction) of the laser beam focus zone.

According to another embodiment of the invention, a computer software product is provided which comprises computer software instructions which, if loaded into a data memory means of a computer, are suitable for controlling functions of the simulation means according to the invention of the above-described apparatus according to other aspects of the invention.

According to yet another embodiment of the invention, a laser materials processing and measurement device is provided which comprises an above-described apparatus for operating the device. According to the invention the apparatus comprises simulation means for simulating operation of the laser materials processing and measurement device and/or the user control means.

According to still another embodiment of the invention, a method is provided for operating a laser materials processing and measurement device with a controllable laser for generating a laser beam and beam control means for adjusting in three spatial directions, in particular in biological tissue. According to the invention, the method comprises loading an above-described computer software product into a data memory means of a computer and/or executing computer software instructions of the computer software product which simulate operation of the laser materials processing and measurement device.

According to yet another embodiment of the invention, a method is provided for operating a laser materials processing and measurement device with a controllable laser for generating a laser beam and beam control means for adjusting the focus zone of a controlled portion of the laser beam in three spatial directions, in particular in biological tissue. The method comprises:

providing an apparatus in accordance with the teachings of the invention, and simulating operation of the laser materials processing and measurement device with one or more of the following functions of the laser materials processing and measurement device:

setting and/or verifying basic settings of the laser materials processing and measurement device, predetermined types of calibration for the laser materials processing and measurement device, predetermined beam control tests for the beam control means of the laser materials processing and measurement device, predetermined materials processing operations, in particular predetermined surgical operations, which may be performed by the laser materials processing and measurement device, predetermined beam deflection functions, which may be performed by the beam control means, predetermined service functions of the laser materials processing and measurement device, outputting of error codes of the laser materials processing and measurement device, for example from an error file of the laser materials processing and measurement device, monitoring and/or complying with predetermined limit values for operating parameters of the laser materials processing and measurement device, for example by means of a limit value file of the laser materials processing and measurement device, in- and/or outputting of predetermined system operating parameters with regard to operation of the laser materials processing and measurement device, for example using an operating parameter register of the laser materials processing and measurement device, and outputting of predetermined system status parameters of the laser materials processing and measurement device, for example from a status parameter register of the laser materials processing and measurement device.

With the above-stated methods, the same advantages may be achieved as with the above-described apparatus for operating the laser materials processing and measurement device according to other embodiments of the invention.

The embodiments of the method of the present invention provide for simulation of one or more functions of the laser materials processing and measurement device even when the laser materials processing and measurement device is not operationally ready and/or not connected to the interface.

BRIEF DESCRIPTION OF THE DRAWINGS

Further options for configuring the apparatus or the method according to the invention are revealed by the following detailed description of given embodiments. These are described with reference to the attached drawing in which:

FIG. 5 shows a view of a display means of an overall structure of a user interface generated by the simulation means of the apparatus of FIG. 2.

FIG. 6 shows a subsection of the user interface of FIG. 5 which is suitable for setting and/or verifying basic settings of the laser materials processing and measurement device of FIG. 2.

FIG. 12 shows a part of the user interface of FIG. 5 which is suitable for outputting error codes from an error file of the laser materials processing and measurement device.

FIG. 14 shows a part of the user interface of FIG. 5 which is suitable for in- and/or outputting predetermined system operating parameters relating to the operation of a laser materials processing and measurement device.

DETAILED DESCRIPTION

Figure 1:
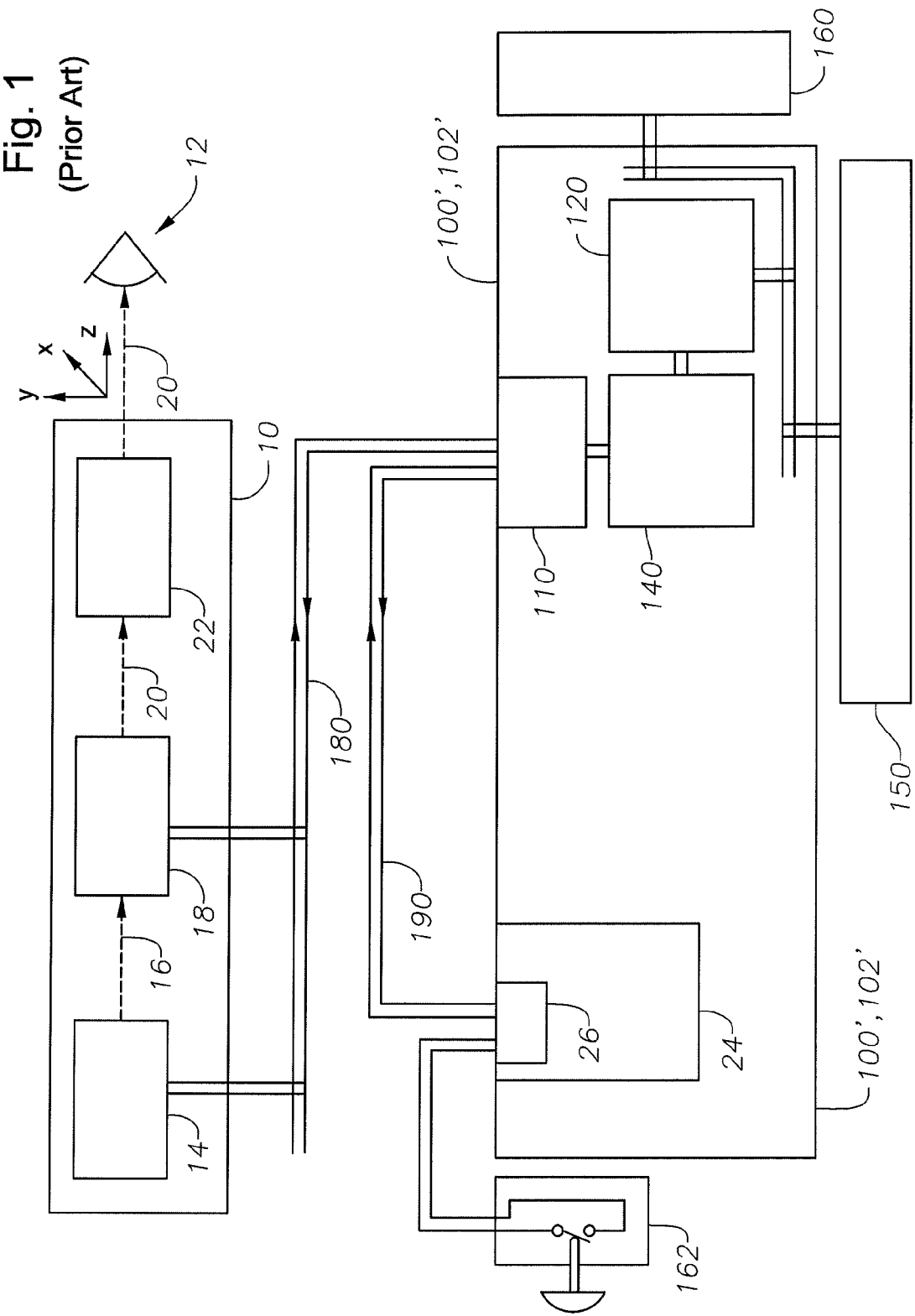
FIG. 1 shows a system for materials processing and measurement using a laser, with an apparatus for operating a laser materials processing and measurement device.

FIG. 1 shows a known system for materials processing and measurement with a laser, wherein the components intended directly for generating the laser beam 16 (laser 14), for adjusting the focus zone of the laser beam 16 in three spatial directions X, Y and Z (beam control means 18) and for forming or focusing the controlled portion 20 of the laser beam (objective lens device 22) are combined in a laser materials processing and measurement device 10, and wherein the components for operating, controlling and monitoring the device 10, such as for instance input means 160 for inputting for example control commands by a user, display means 150 in particular for displaying the operating state and the input control commands, user control means 120 for processing the user inputs and driving the display means 150, for relaying user control commands and command sequences and/or for retrieving operating state information for the device 10 and further system-specific control means 24 and/or input means, such as for instance the user switch 162, and an interface 110 for bidirectional data transfer to the device 10 are combined in a second unit, namely the control device 100 equipped as a computer 102 with corresponding peripherals 150, 160, 162. The system shown in FIG. 1 is known per se and has been described above in relation to the explanation of the problem to be solved by the embodiments of the present invention.

Figure 2:
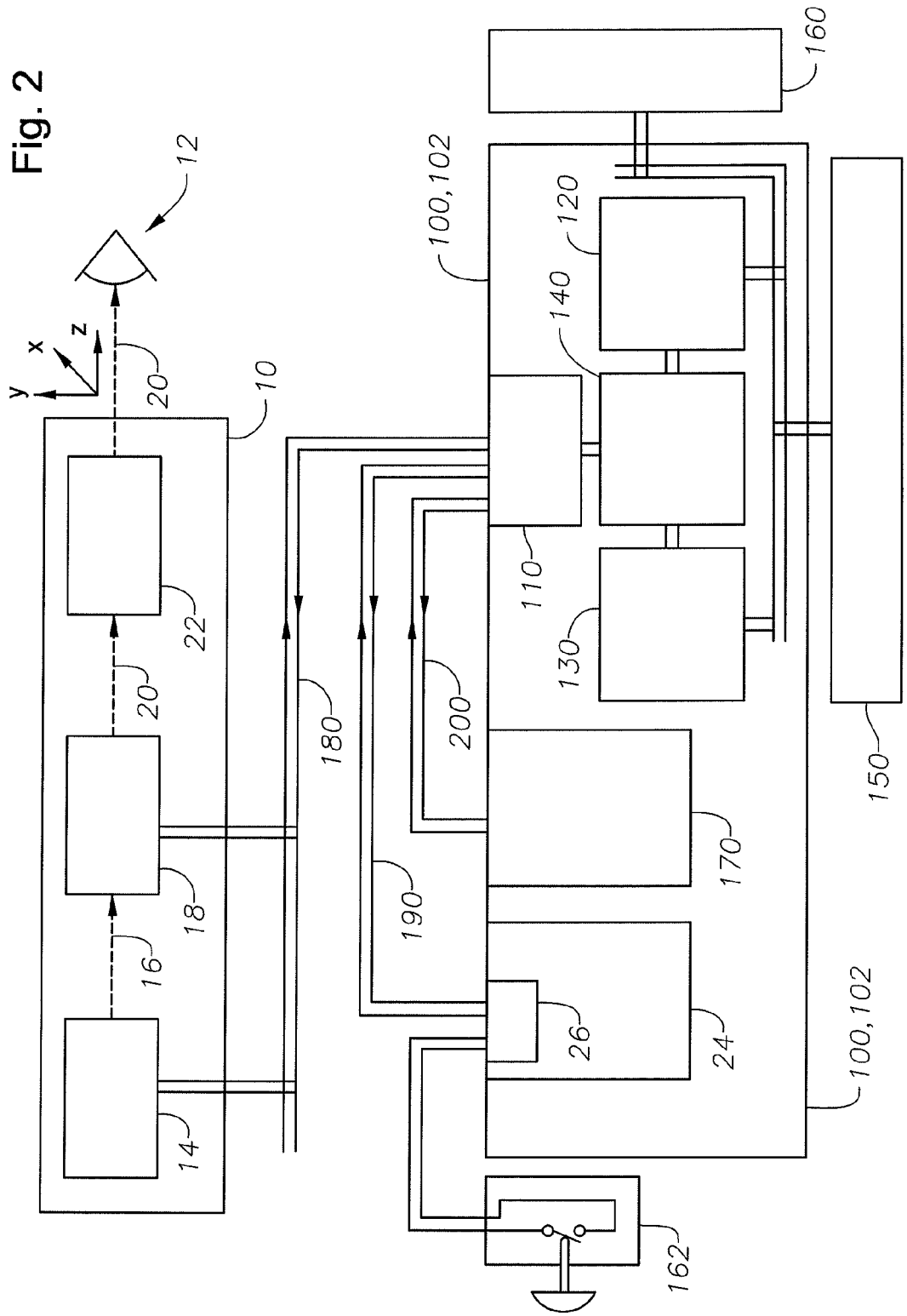
FIG. 2 shows a further development according to the invention of the system of FIG. 1, with the simulation means and the additional testing means according to the invention.

FIG. 2 now shows an exemplary embodiment of an apparatus 100 according to an aspect of the invention, obtained as a further development of the apparatus 100' shown in FIG. 1. In FIG. 2 components with similar or the same functions as in FIG. 1 are designated with the same reference numerals. Only differences, modifications and alternative embodiments of the apparatus according to the invention 100 are explained below with reference to the apparatus 100' shown in FIG. 1.

In the system shown in FIG. 2 for materials processing and for measuring with a laser, the apparatus 100 for operating the laser materials processing and measurement device 10 comprises according to the invention, in addition to the interface 110 already described with reference to FIG. 1, the user control means 120, the input means 160 and the system-specific input means, such as the user switch 162, the system-specific control means 24 and the display means 150, simulation means 130 for simulating operation of the laser materials processing and measurement device 10 and/or of the user control means 120 and optional testing means 170 for simulating data transfer functions of the control means 24.

In order to test the functionality and operation of the apparatus 100 for operating the laser materials processing and measurement device 10, including all the components 110, 120, 140, 150, 160, 162 and 24 belonging to the apparatus 100, irrespective of the provision or operational readiness of the device 10, the simulation means 130 has to model or simulate all the functions of the system-specific user control means 120 and the interplay of the user control means 120 with all the components connected or in data exchange therewith (i.e. the laser 14, the beam control means 18 and any status files or registers of the device 10, such as for instance an error code file, a limit value file, an operating parameter register and a status parameter register of the device 10) and the components belonging to the apparatus 100 or the computer 102 (i.e. the input means 160, the display means 150, the system-specific control 24, the system-specific input means 162, the interface 110 and the command library 140). So that this is possible even if no bidirectional data exchange is taking place with the device 10 via the first bidirectional data link 180, the simulation means 130 also comprises testing means 170 for simulating data transfer functions of the laser materials processing and measurement device 10 and for simulating data transfer functions of the system-specific control means 24. If the apparatus 100 is implemented in the form of a computer 102, the testing means 170 may advantageously be configured as a plug-in board for the computer 102, like the system-specific control means 24.

Figure 3:
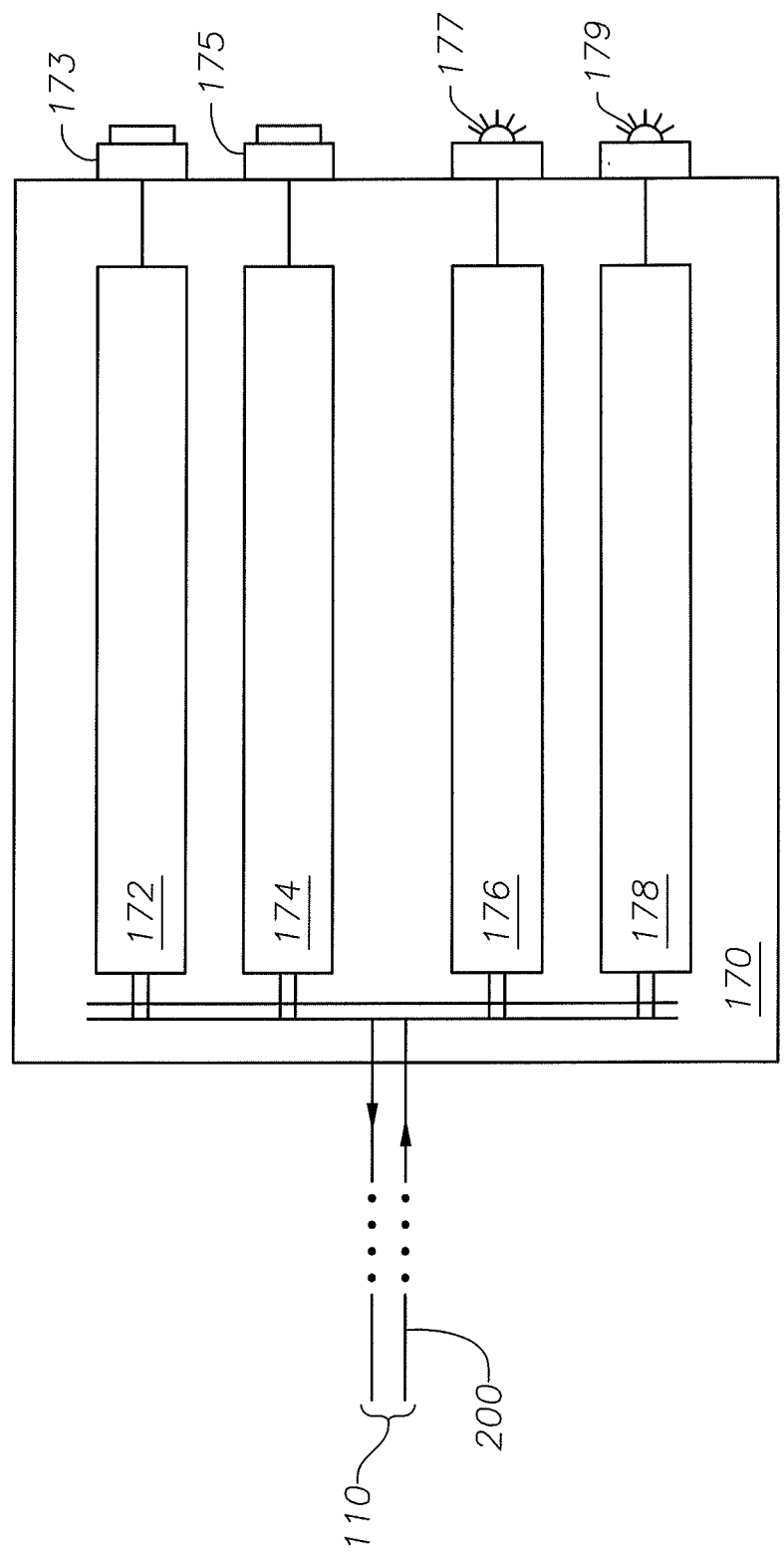
FIG. 3 shows a configuration of the testing means suitable for simulating a user switch and for simulating the execution of laser energy changes.

FIG. 3 is a schematic representation of a logical structure of the exemplary testing means 170 in the form of a plug-in board. The testing means 170 shown in FIG. 3 comprise the following logical elements: means 172 for simulating operation of the system-specific input means, in particular of the user switch 162, means 174 for simulating the energy change of the laser beam 16 and in particular of the bidirectional data transfer 180, necessary for energy change, between the laser 14 and the interface 110, means 176, 177 for displaying that a beam control command sequence brought about by interactive user input has been loaded into the beam control means 18, and means 178, 179 for displaying simulated feedback from the device 10, for example output information from the beam control means 18, to the effect that an energy change of the laser beam 16 is necessary for the purposes of executing a beam control command sequence.

Depending on the configuration of the system-specific input means 162, the simulation means 170 comprises corresponding input means 173 of identical function but compact configuration and associated drive electronics 172. If the system-specific input means are configured as a user switch 162, the input means may be configured as a first momentary-contact switch 173. If the system-specific input means is configured as a system-specific energy change switch or controller, the input means 173 may be configured for example as a toggle switch or as a potentiometer.

The means 174, 175 for simulating the energy change of the laser beam 16 simulate the corresponding part of the bidirectional data transfer between the interface 110 and the laser 14 via a first bidirectional data transfer link 180 between the interface 110 of the apparatus 100 and the device 10. If, for example, in regular operation of the user control means 120 feedback is expected from the laser 14 to the effect that the laser 14 has performed the desired energy change of the laser beam 16, the simulation means 174, 175 may be configured as a second momentary-contact switch 175 actuatable by the user carrying out the test and corresponding drive electronics 174 therefor. Actuation of the second momentary-contact switch 175 corresponds to, and generates the same, feedback signals as those generated by the laser 14 after the laser has performed the energy change of the laser beam 16.

The display means 176, 177 for the loading status of a control command sequence in the beam control means 18 substantially have the task of displaying binary information, namely whether or not the control command sequence has been completely loaded into the beam control means 18. Consequently, the display means 176, 177 may for example simply take the form of a first indicator light 177, such as for instance an LED, with corresponding drive electronics 176 therefor. Illumination of the first indicator light 177 corresponds to feedback from the beam control means 18 about successful and complete loading of a beam control command sequence.

The display means 178, 179 for simulating feedback from the device 10 to the effect that an energy change is needed for the purposes of executing a beam control command sequence may in turn be configured in the testing means 170 simply as a binary data display. To this end the display means 178, 179 are configured in the testing means 170 simply as a second indicator light 179, in particular a second LED with corresponding drive electronics 178 therefor. Illumination of the second indicator light 179 simulates receipt of feedback from the device 10 to the effect that an energy change of the laser beam 16 is necessary.

Figure 4:
FIG. 4 shows a command sequence control procedure, with a laser energy change using testing means of FIG. 3.

FIG. 4 shows by way of example a control procedure for a control command sequence, in which after a first laser materials processing sequence, for example an ophthalmic surgery bed cut, an energy change of the laser beam 16 is necessary for a subsequent second laser materials processing sequence, for example an ophthalmic surgery side cut. In step 1 shown in FIG. 4 a signal of a system status parameter register of the device 10 indicates that a command control sequence ("Data") has been completely and successfully loaded in the beam control means 18 ("scanner") ("Data in scanner" signal=High). In control step 2 an output variable of the system status parameter register indicates that the beam control means 18 are ready to execute a beam control sequence ("Scan") ("Scan enable"=High). The operational readiness of the beam control means 18 is displayed for the purposes of simulation in the testing means 170 by illumination of the first indicator light 177. The first laser materials processing sequence, in this case a bed cut, is then performed.

Once a bed cut has been successfully performed, an energy change is necessary. Accordingly, in control step 3 a binary variable is implemented in a system status parameter register ("Energy change" variable=High). In control step 4 the variable for displaying the readiness status of the beam control means 18 is implemented in the system status parameter register ("Scan enable"=Low). The apparatus 100 must now transmit the command for changing the energy of the laser beam to the laser 14 of the device 10 and wait for feedback or confirmation from the laser 14 to the effect that the energy of the laser beam 16 has been successfully changed. Accordingly, the second indicator light 179 lights up on the testing means 170.

To simulate successful performance of the energy change of the laser beam, the user performing the test presses the second momentary-contact switch 175 of the testing means. Feedback to the effect that the laser beam energy has been successfully changed is simulated by pressing the second momentary-contact switch 175 and would in normal operation cause the beam control means 18 to output the feedback that it is once again operationally ready. This is displayed in control step 6 by setting the corresponding binary variable in the system status parameter register and simulated for the purposes of simulation by illumination of the first indicator light 177 of the testing means 170 (meaning of illumination of indicator light 177: "Scan enable" variable=High).

In control step 7 the resetting of a system status parameter of the register variables which would follow in normal operation is represented for the purposes of simulation in the test beam 170 by extinction of the second illuminated means 179 ("Energy change" system status variable reset to Low). In normal operation the second laser materials processing sequence, for example a side cut, would then be performed. In normal operation, at the end of the second sequence all the control commands would be executed in the laser control means 18 and first of all no further control sequence would be loaded. Control step 9 indicates, by setting the corresponding variables in the system status parameter register, that no further command sequence to be executed is loaded (resetting of "Data in scanner" variable=Low). Finally, in control step 10 the feedback needed in normal operation, to the effect that the beam control means 18 are not ready to carry out a control sequence, is displayed by resetting the corresponding variables in the system status parameter register ("Scan enable" is reset to Low).

Figure 5:
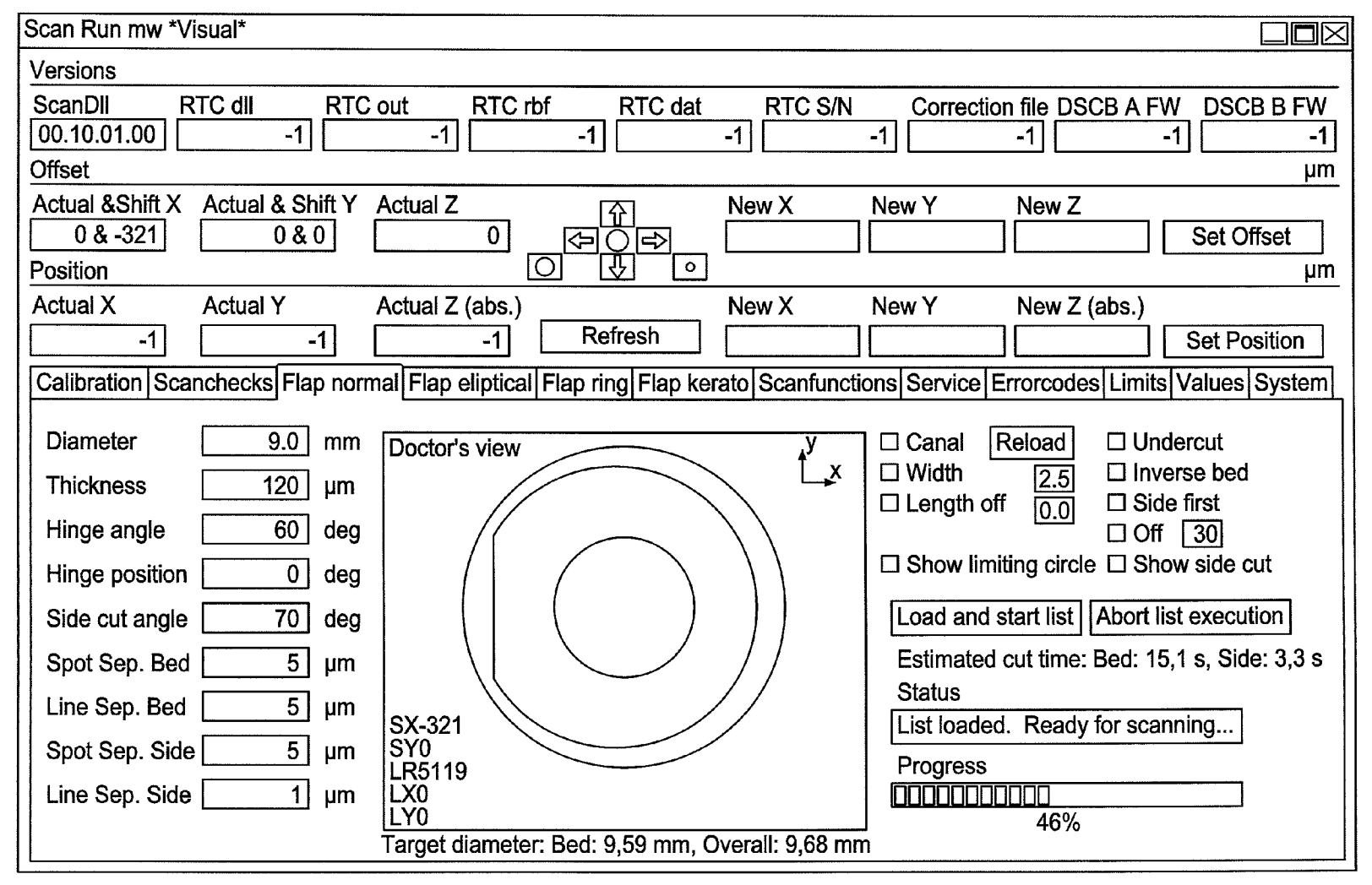
Figure 6:
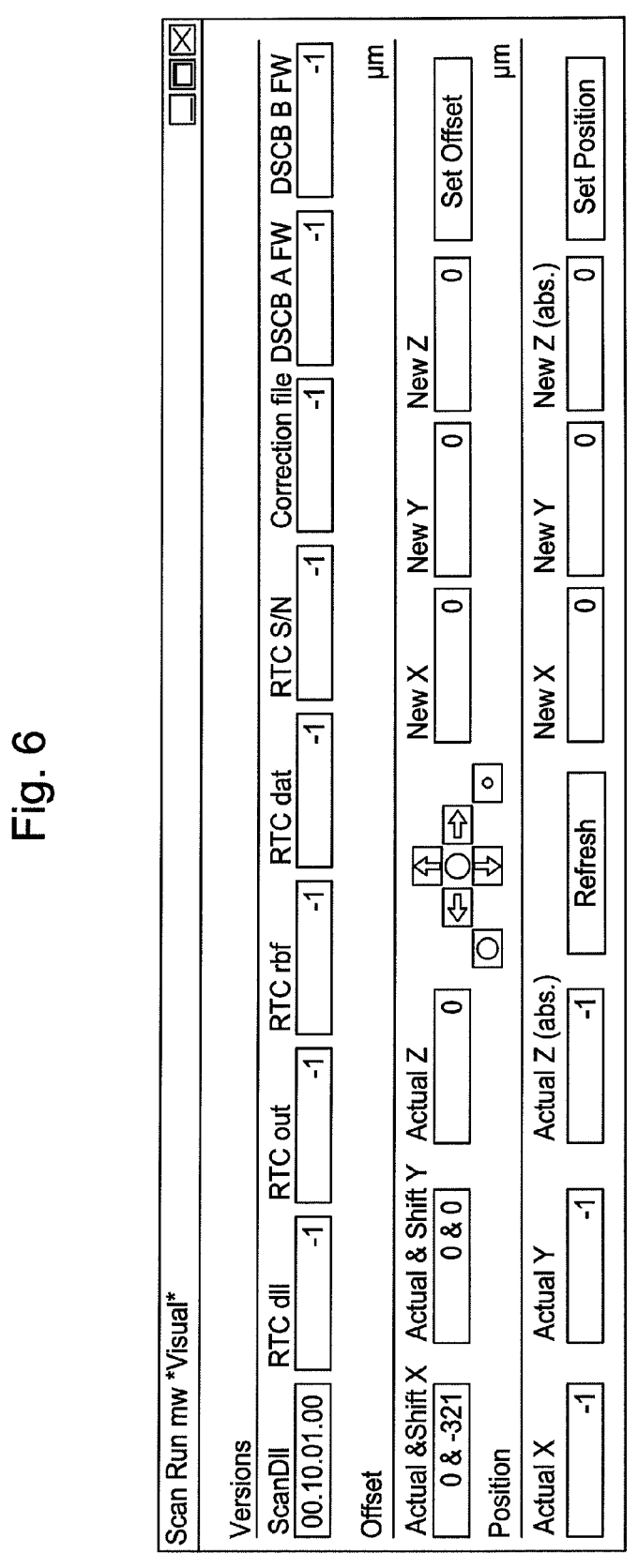

FIG. 5 illustrates by way of example a possible user interface generated by the simulation means 130 on a display of the display means 150, such as for instance on the screen of a computer 102. The top sub-region, shown shaded in FIG. 5, of the user interface is shown separately in FIG. 6. The sub-region shown in FIG. 6 comprises in- and output fields needed for carrying out predetermined service functions of the laser materials processing and measurement device 10, for example the fields shown in the "offset" region and the service function button "Set offset". Moreover, the part of the user interface 6 shown in FIG. 6 comprises predetermined system operating parameters, such as for instance the contents of the variables of an operating parameter register of the device 10, and predetermined system status parameters, such as for instance the variables of a status parameter register of the device 10. In the example shown in FIGS. 5 and 6, the field "Scan dll" shows a version number of the simulation means, the field "RTC dll" a second version number, namely that of the user control means 120 simulated by the simulation means 130, the field "RTC out" the software version number of the user control means 120, the field "RTC rbf" a version number of the system-specific control means 24, the field "RTC dat" a help file used by the system-specific control means 24, the field "RTC S/N" a serial number of the user control means 120, the field "Correction file" a correction file possibly loaded in the user control means 120, the field "DSCB A FW" information relating to the means present in the beam deflection means 18 of the device 10 for deflecting the laser beam laterally (XY module firmware) and the field "DSCB B FB" information relating to the axial focusing device used in the beam control means 18 (Z module firmware). In the "offset" region of the user interface shown in FIGS. 5 and 6, the fields "Actual+Shift X", "Actual+Shift Y", "Actual Z" or "New X", "New Y", "New Z" show current offset of the focus zone of the laser beam in the three spatial directions X, Y and Z, or centring of the laser beam in the lateral X, Y plane. Furthermore, the sub-region of the user interface comprises buttons provided with arrows, a circle and a dot, which allow navigation of the focus zone of the controlled portion 20 of the laser beam 16.

Figure 9:
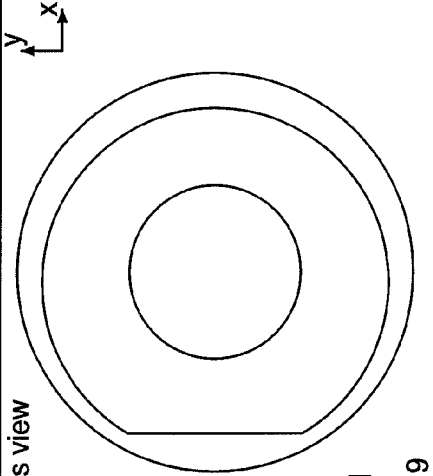
FIG. 9 shows a portion of the user interface of FIG. 5 which is suitable for simulating a predetermined ophthalmological surgical operation, which can be carried out by the laser materials processing and measurement device, namely a "normal flap cut".

In the lighter shaded bottom sub-region of the user interface shown in FIG. 5, which is shown separately in FIG. 9, a user interface is shown, as an example of a predetermined materials processing operation, for a predetermined ophthalmic surgery operation, namely a "normal flap cut ("Flap normal") in the corneal tissue of a human eye. More precisely, the user interface generated by the simulation means 130 is shown for controlling and monitoring the admittedly only simulated operation. The middle region of the lower sub-region (FIGS. 5 and 9) is a schematic diagram of the simulation of a normal flap cut in a plan view of the simulated irradiation field extending in the X, Y plane and achievable by the imagined laser beam. The parameters shown bottom left in the plan view are the values for automatic centring operations in the X or Y directions "SX" and "SY" and the radius "LR" of the limiting circle (this limiting circle is a circle placed around the outermost points of the currently set cutting pattern, which on shifting must not cross the defining circle shown in FIG. 5 in the bottom middle sub-region by the outer dotted circle) and the shifts "LX" or "LY" in the X or Y directions of the centre point of the limiting circle.

Under the plan view the diameter of the bed is indicated with a curvature correction (target diameter: "Bed"), and the diameter of the bed and of the side cut with curvature correction (target diameter "Overall"). In the fields in the region to the left of the plan view of the simulated flap cut, the following parameters of the normal flap cut, programmable by the user, are indicated from top to bottom. These are: the flap diameter ("Diameter"), the flap thickness ("Thickness"), the opening angle of the flap hinge ("Hinge angle"), a shift of the hinge along the flap diameter ("Hinge position"), a cut angle of the side cut ("Side cut angle"), spot spacing in the bed cut ("Spot Separation Bed"), line spacing in the bed cut ("Line Separation Bed"), spot spacing in the side cut ("Spot Separation Side"), line spacing in the side cut ("Line Separation Side").

The region to the right of the plan view of the simulated flap cut shows the following: a parameter, which indicates whether or that the bed cut is being carried out as a full circle ("Undercut"), a parameter which indicates that or whether the bed cut is started relative to the hinge position ("Inverse bed"), a parameter which indicates whether the limiting circle is to be indicated ("Show limiting circle"), a parameter which indicates that or whether the side cut takes place before the bed cut ("Side first"), a parameter which indicates whether a canal is to be cut from the maximum cutting region to the bed ("Canal"), the width of the optional canal ("Width"), the offset of the canal from the maximum deflection region ("Length off"), and a parameter which indicates whether the graphics displays or should display the side cut ("Show side cut"), execution times, calculated for the purposes of simulation, for the bed cut ("15.1 s") and for the "side cut" ("3.3 s"), a status field with the name "Status", which indicates whether or not the command sequence has been loaded in the beam deflection means 18 ("List loaded"), and information as to whether or not the beam deflection means 18 and focusing means 22 are ready for scanning or cutting ("Ready for scanning").

Similarly, the simulation means 130 may also generate user interfaces for other predetermined materials processing operations or laser cutting sequences as simulation of that which the user control means 120 would generate. In the example shown in FIG. 5 of the user interface of a simulation means 130 for a system for carrying out ophthalmic surgery operations, these are user interfaces for an elliptical flap cut ("Flap elliptical"), an annular flap cut ("Flap ring") and a keratome flap cut ("Flap kerato"). It is not essential to understanding of the invention to explain the corresponding user interfaces in detail. A description thereof will therefore be omitted.

Figure 7:
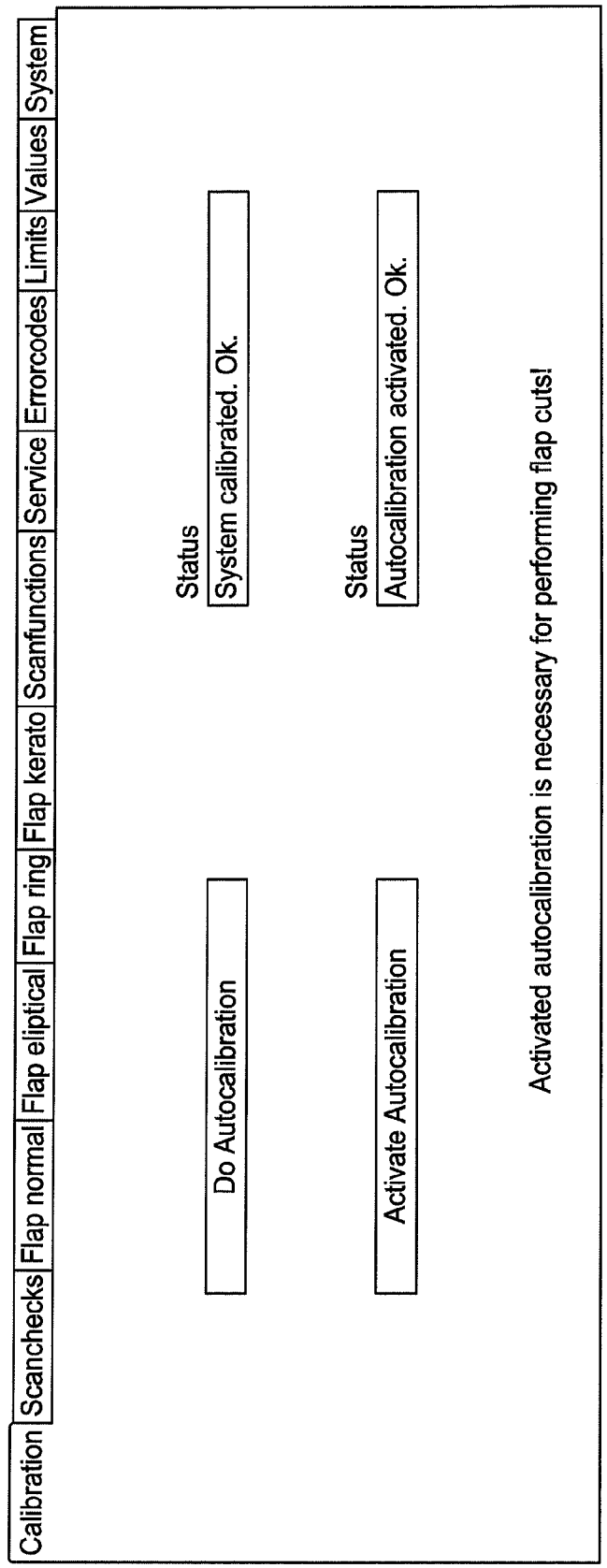
FIG. 7 shows a portion of the user interface of FIG. 5 which is suitable for simulating predetermined calibration functions of the laser materials processing and measurement device of FIG. 2.

The simulation means 130 may also be configured for simulating various methods for calibrating the laser materials processing and measurement device 10. In this respect, FIG. 7 shows by way of example the user interface simulated by the simulation means 130 for calibration functions of a system for ophthalmic surgery. The bottom region contains the note which the user control means 120 would also generate, namely that "Activated auto calibration is necessary for performing flap cuts". A bottom button in the left-hand region of the user interface shown in FIG. 7 allows activation of a predetermined calibration function ("Activate auto calibration"). An associated status output window in the right-hand region shows system status confirmation about successfully performed activation of the auto calibration function ("Auto calibration activated. OK"). A top button in the left-hand region allows start-up of the auto calibration process for the purposes of simulation ("Do auto calibration"). An associated status output window in the right-hand region shows system feedback about successfully performed auto calibration function ("System calibrated. OK.").

Figure 8:
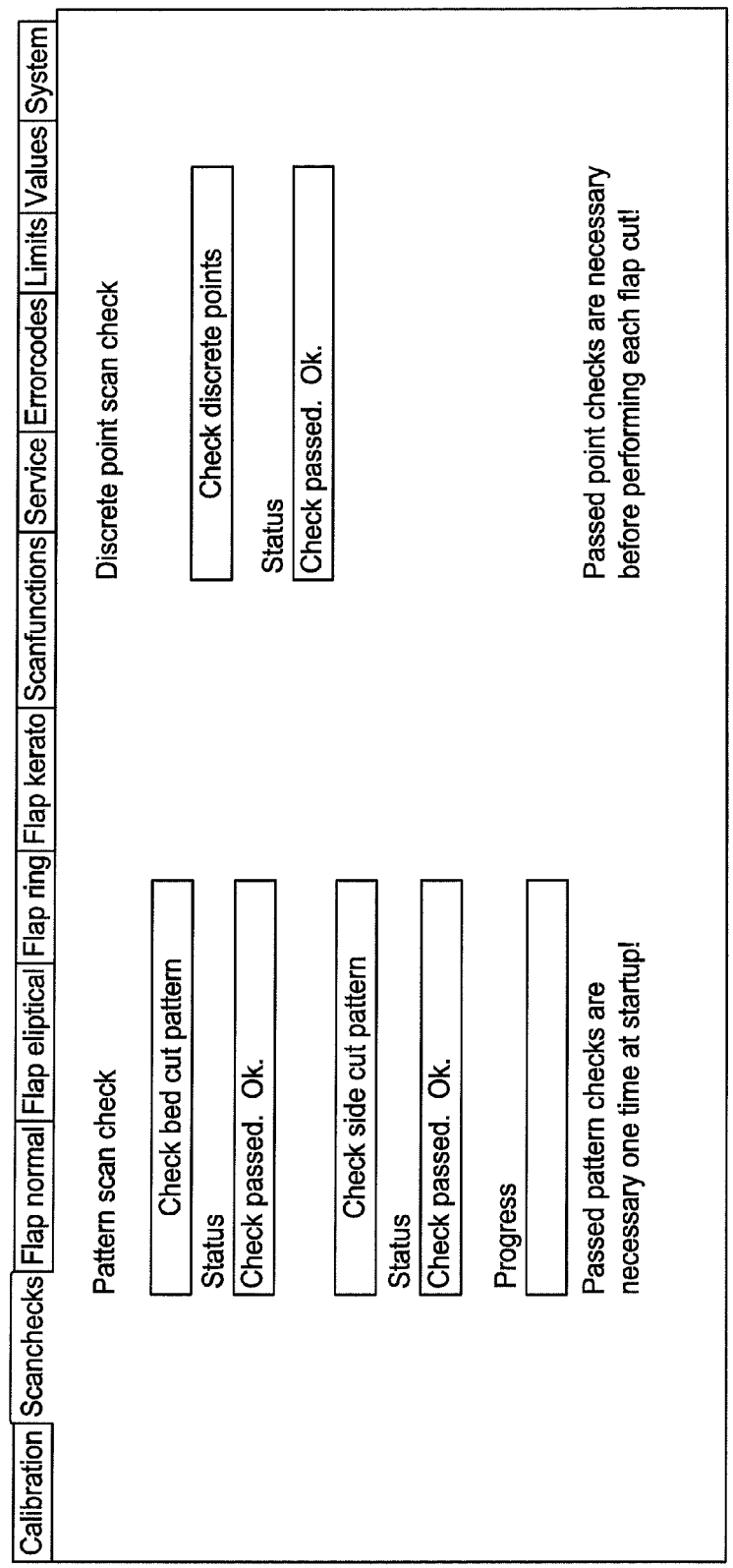
FIG. 8 shows a portion of the user interface of FIG. 5 which is suitable for predetermined beam control tests of the beam control means and/or predetermined beam deflection functions, which may be performed by the beam control means.

As an example of the simulation of predetermined beam control tests of the beam control means 18 of the device 10, FIG. 8 shows, in an ophthalmic surgery system by way of example, a user interface simulated by the simulation means 130 for specific beam deflection tests with the designations bed cut pattern ("Check bed cut pattern"), side cut pattern ("Check side cut pattern") and discrete points ("Check discrete points").

Figure 10:
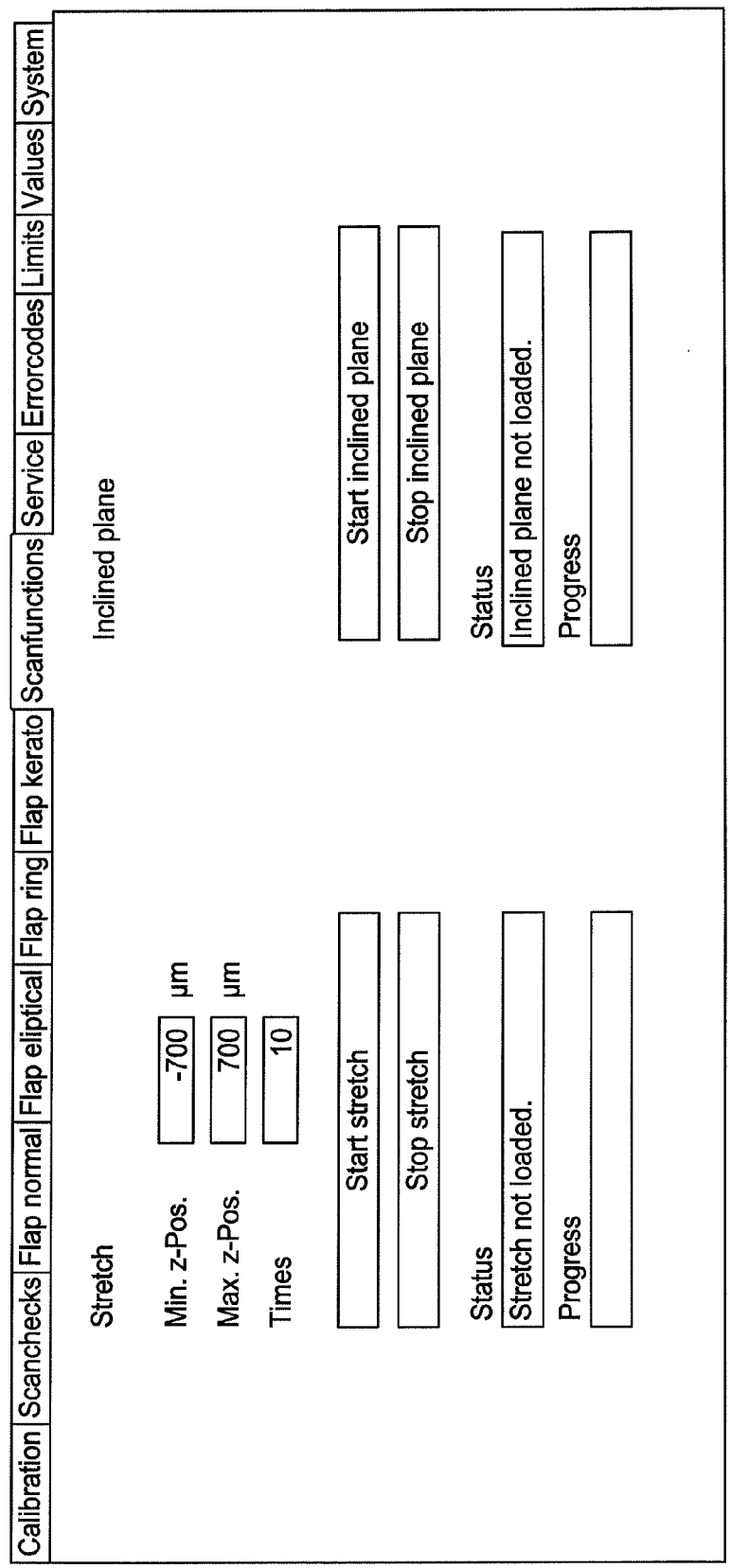
FIG. 10 shows a portion of the user interface of FIG. 5, wherein a function of the "Z-stretch" type and a function of the "inclined plane" type are provided in the simulation as predetermined beam deflection functions, which may be performed by the beam control means.

As an example of predetermined beam deflection functions, which may be executed by the beam control means, FIG. 10 shows, in relation to the example of an ophthalmic surgery system for the purposes of simulation, operations which are executed by the objective lens device 22. To test the optical system 22, which may be a beam expanding optical system, for the purposes of simulation the left-hand region of the user interface shown in FIG. 10 shows the user-programmable parameters and control buttons necessary for performing "Z-Stretch" and a status output field. In the right-hand part of FIG. 9 the control buttons and the status output field are shown for an adjustment function of the "Inclined plane" type. This adjustment function comprises an oblique bed cut, a flat side cut and two reference lines extending in the Z-direction. As with the user control means 120 working during actual operation, in operation of the simulation means 130 the "inclined plane" adjustment function may be started for the purposes of simulation by the user by pressing the button "Start inclined plane" and interrupted at any time during execution by pressing a button "Stop inclined plane".

Figure 11:
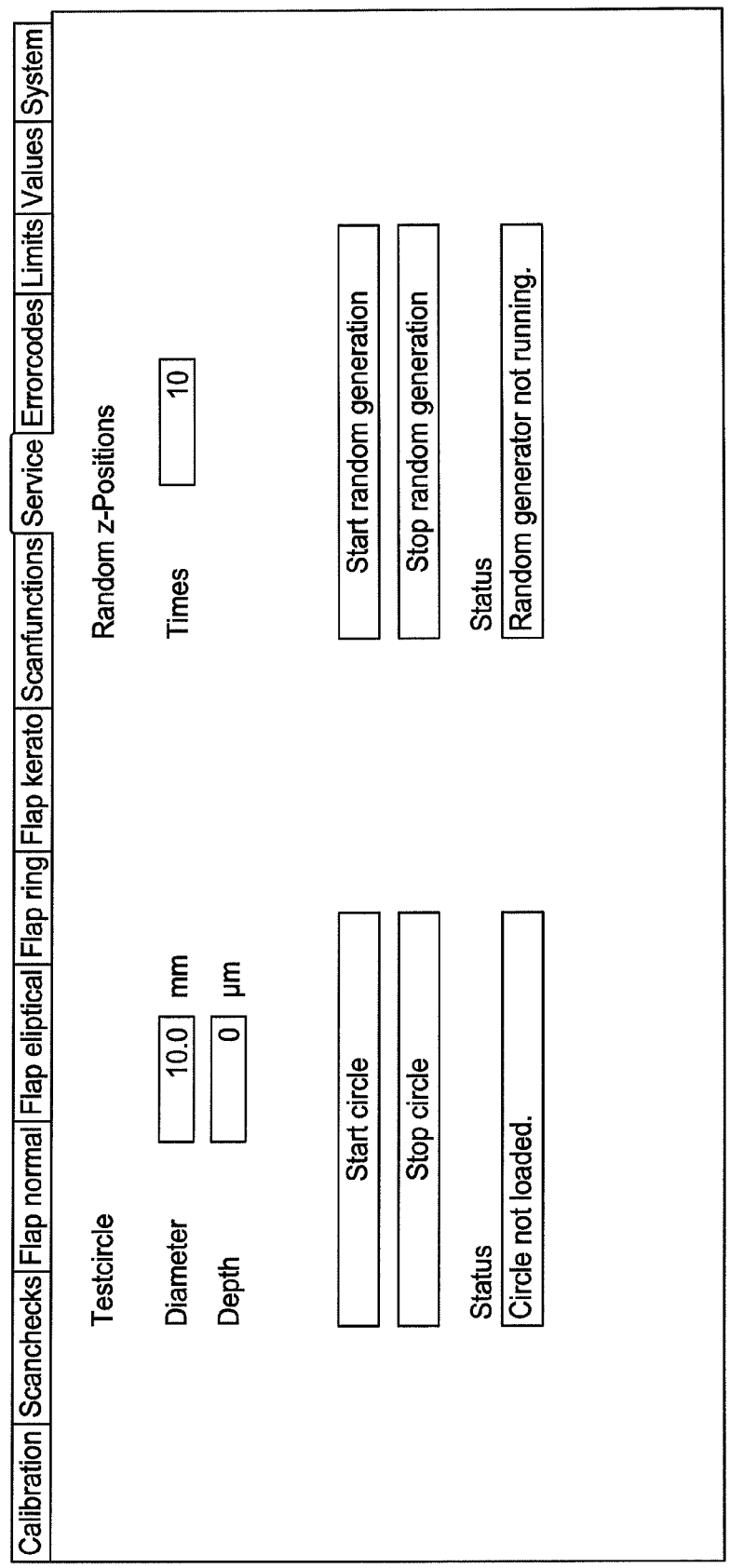
FIG. 11 shows a portion of the user interface of FIG. 5, wherein a function for carrying out or cutting a test circle and/or a function for adjusting a series of randomly selected axial position changes of the focus zone of the laser beam are provided as predetermined service functions of the laser materials processing and measurement device.

As an example of simulation of predetermined service functions of the laser materials processing and measurement device 10, FIG. 11 shows, for the example of an ophthalmic surgery system, a first explicit service function of the "test circle" type, with any desired diameter programmable by the user ("Diameter") and any desired programmable cut depth ("Depth"), and a second service function for producing a randomly determined sequence of positions to be which the laser beam is to be moved ("Random Z-Positions"). The latter relates in the example to randomly selected depths (i.e. positions in the Z-direction) of the beam focus of the controlled portion 20 of laser beam 16. The number ("Times") of the positions to be randomly generated may be programmed by the user.

As an example of simulation of the output of error codes of the laser materials processing and measurement device 10, FIG. 12 shows a user interface simulated by the simulation means 130, as would also be generated in real operation by the user control means 120, for output of error codes. In particular, in the simulated user interface the contents of an error code file of the device 10 are displayed with means for moving the viewing window over the file contents (scrolling).

Figure 13:
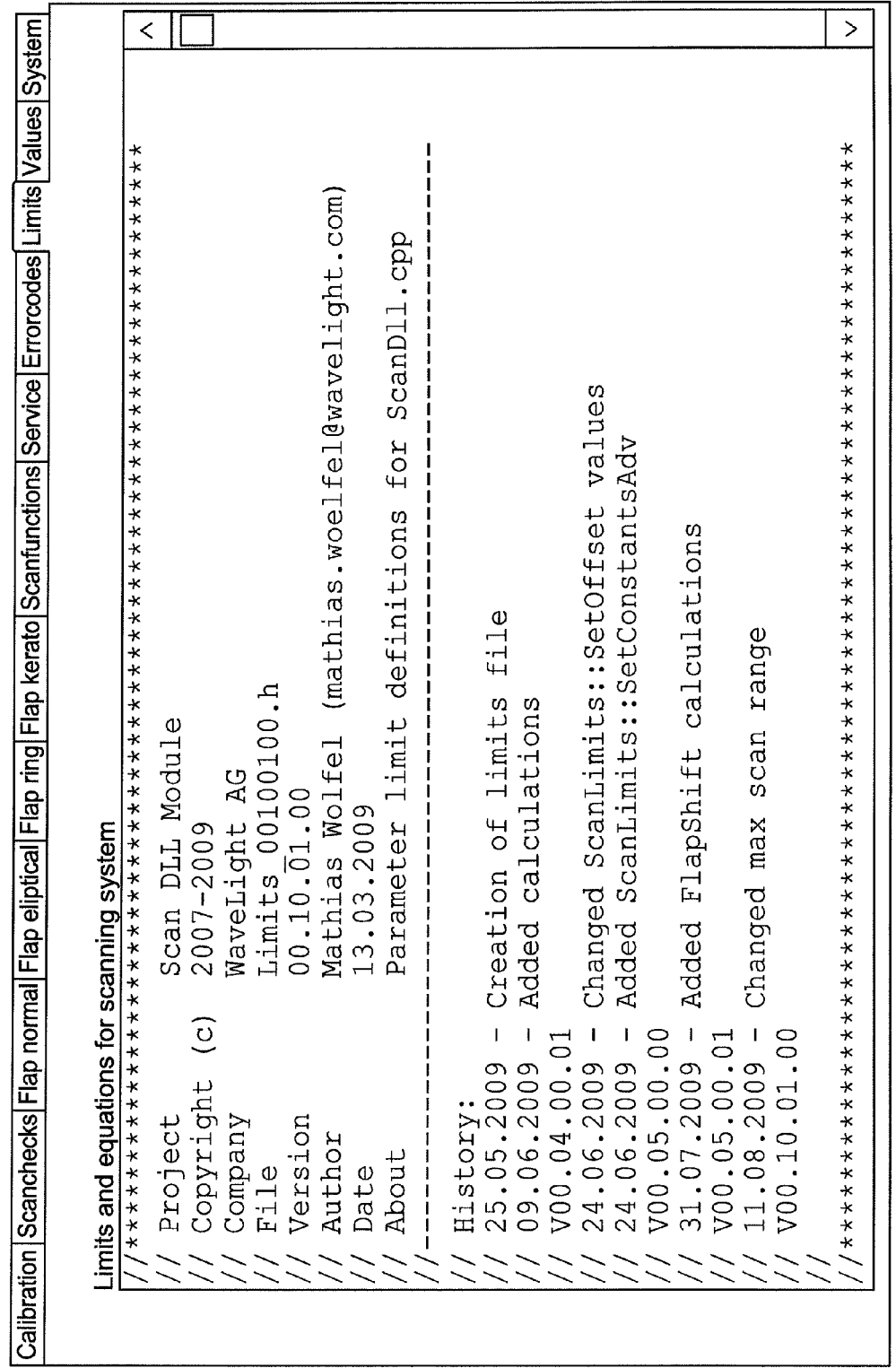
FIG. 13 shows a part of the user interface of FIG. 5 which is suitable for displaying and/or processing predetermined limit values from a limit value file of the laser materials processing and measurement device for monitoring and/or complying with limit values of operating parameters of the device.

As an example of in- and/or outputting of predetermined system operating parameters relating to simulated operation of the device 10, FIG. 13 shows a user interface generated by the simulation means 130, as would also be generated in real operation by the user control means 120.

As an example of in- and/or outputting of predetermined system operating parameters relating to simulated operation of the device 10, FIG. 14 shows, for the example of an ophthalmic surgery system, the user interface simulated by the simulation means 130 for display and user programming of individual elements of an operating parameter register of the device 10. The simulated elements, shown in FIG. 14, of the operating parameter register comprise scaling factors (to be indicated in bits per mm) for the lateral X-Y direction and for the Z direction ("Scale XY" "Scale Z"), the laser pulse frequency (to be indicated in kHz) ("laser frequency"), travel speed (to be indicated in bits/ms) for shifting of the laser focus zone in the material to be processed ("Goto speed"), a jump speed in Z-direction (to be indicated in bits/ms) ("Stretch speed"), a maximum focus jump speed (to be indicated in bits/ms) ("Maximum jump speed"), a mark shift speed for testing predetermined beam patterns (to be indicated in bits/ms) ("Check speed"), a mark shift speed (to be indicated in bits/ms) ("Logo speed"), a waiting time after mark commands (to be indicated in 10 μs) ("Mark delay"), a waiting time after jump commands (to be indicated in 10 μs) ("Jump delay"), a laser on delay before mark commands (to be indicated in 10 μs) ("laser-on delay") and a laser off delay after mark commands (to be indicated in 10 μs) ("laser-off delay").

Figure 15:
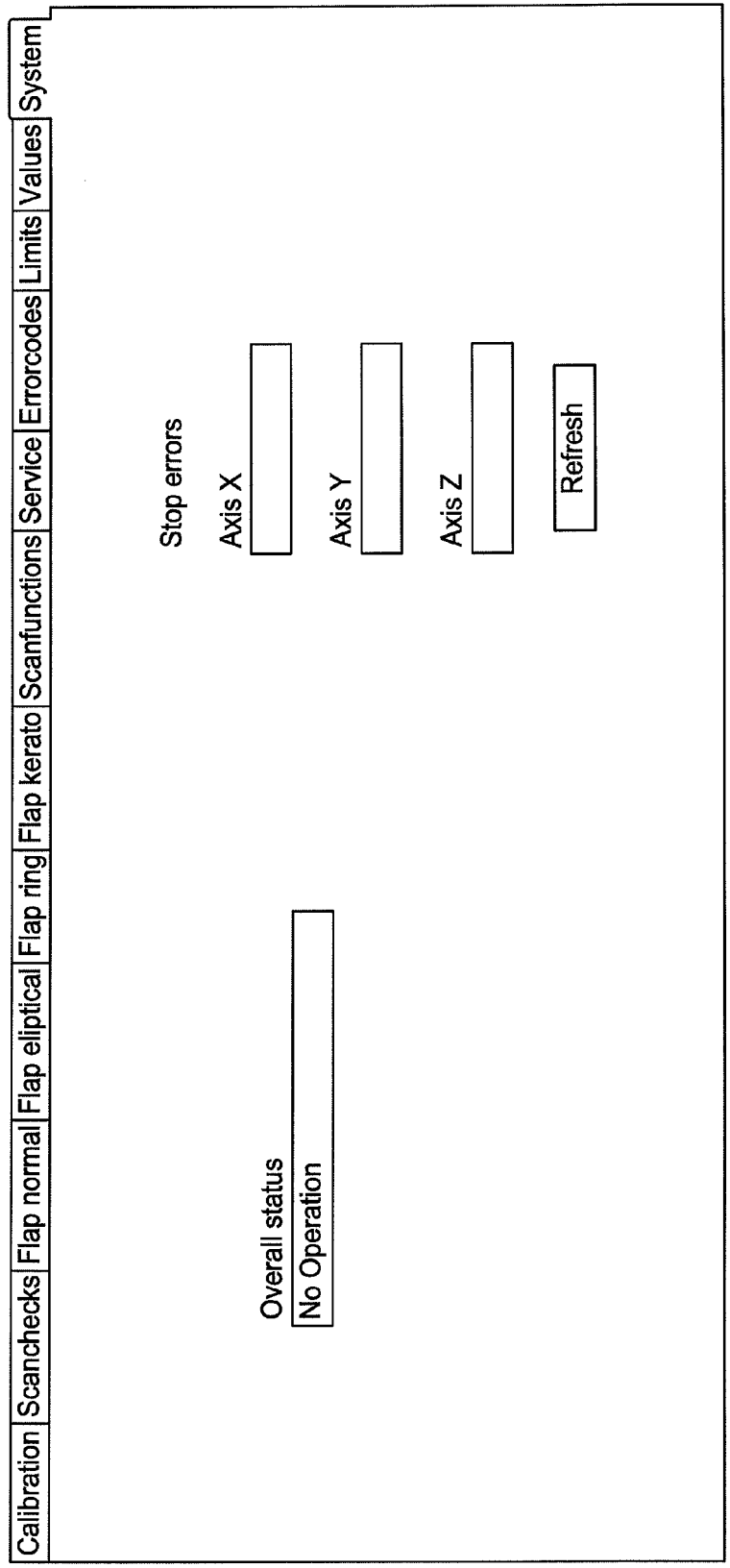
FIG. 15 shows a part of the user interface of FIG. 5 which is suitable for outputting predetermined system status parameters of the laser materials processing and measurement device.

Finally FIG. 15 shows as an example of simulated outputting of predetermined system status parameters of the device 10, for the example of the ophthalmic surgery system, the fields shown by the simulation means 130 on the user interface for outputting elements of a status parameter register, in the same way as these would be displayed in real operation of the user control means 120. These comprise an indication of the operating status of the system or of the device 10 with regard to the operations or processes in all categories or "tabs" of the user interface ("Overall status"), and display which error type ("Stop errors") has triggered a stop event in the direction of the X, Y and Z axes.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

The invention claimed is:

1. An apparatus for operating a laser materials processing and measurement device with a controllable laser for generating a laser beam and beam control means for adjusting the focus zone of a controlled portion of the laser beam in three spatial directions, in particular in biological tissue, having:
    an interface for operating a first bidirectional data transfer link with the laser and the beam control means,
    user control means for inputting and displaying control commands or control command sequences and for controlling operation of the laser materials processing and measurement device, and
    simulation means for simulating data transfer that simulates operation of the laser materials processing and measurement device or of the user control means, the simulation means configured to simulate the data transfer that occurs along the data transfer link when the device is connected to the interface, of a feedback signal generated by the laser after performing the operation, the simulation means configured to simulate the data transfer even when the device is not connected to the interface.

2. An apparatus according to claim 1 further comprising:
    display means for displaying input screens for the control commands, the control command sequences, or information relating to the operation of the laser materials processing and measurement device, and
    input means for inputting the control commands, the control command sequences, or the information relating to the operation of the laser materials processing and measurement device.

3. An apparatus according to claim 1, furthermore comprising:
    a command library for providing the control commands or the control command sequences to the interface.

4. An apparatus according to claim 1, wherein the simulation means furthermore comprises testing means for simulating processes or operating sequences of the device.

5. An apparatus according to claim 4, furthermore comprising:
    control means for driving the beam control means, wherein
    the interface is configured to operate a second bidirectional data transfer link with the control means, and
    the testing means are configured to simulate data transfer functions of the control means or the laser materials processing and measurement device.

6. An apparatus according to claim 5, wherein
    the control means comprises a user switch for switching the beam control means on or off, and
    the testing means comprise one or more of the following elements:
        the simulation means configured for system-specific input means, such as for instance a user switch,
        the simulation means configured for an energy change of the laser beam,
        display means for a loading status of a beam control command sequence,
        display means for beam control output information, in particular for information indicating that energy change is necessary.

7. An apparatus according to claim 1, wherein the simulation means are configured to simulate one or more of the following functions of operation of the laser materials processing and measurement device:
    basic settings of the laser materials processing and measurement device,
    predetermined types of calibration for the laser materials processing and measurement device,
    predetermined beam control tests for the beam control means of the laser materials processing and measurement device, predetermined surgical operations performed by the laser materials processing and measurement device, predetermined beam deflection functions performed by the beam control means, predetermined service functions of the laser materials processing and measurement device, error codes of the laser materials processing and measurement device, predetermined limit values for operating parameters of the laser materials processing and measurement device, predetermined system operating parameters with regard to operation of the laser materials processing and measurement device, and predetermined system status parameters of the laser materials processing and measurement device.

8. An apparatus according to claim 7, wherein the laser materials processing and measurement device is a device for performing surgical operations and for carrying out measurements on a human eye.

9. An apparatus according to claim 7, wherein the predetermined beam control tests or the predetermined beam deflection functions comprise beam control for a bed cut and for a side cut.

10. An apparatus according to claim 7, wherein the predetermined surgical operations comprise a normal flap cut, an elliptical flap cut, a flap ring cut, a flap cut or a keratoplasty.

11. An apparatus according to claim 7, wherein the predetermined beam deflection functions comprise a "Z-stretch" function and an "inclined plane" function.

12. An apparatus according to claim 7, wherein the predetermined service functions comprise a function for carrying out or cutting a test circle or a function for adjusting a series of randomly selected axial position changes of the focus zone of the laser beam.

13. A computer software product with computer software instructions, which, when loaded into a data memory means of a computer, are suitable for controlling functions of the simulation means of the apparatus according to claim 1.

14. A laser materials processing and measurement device, comprising an apparatus according to claim 1.

15. A method for operating a laser materials processing and measurement device with a controllable laser for generating a laser beam and beam control means for adjusting the focus zone of a controlled portion of the laser beam in three spatial directions, in particular in biological tissue, the method comprising:

loading a computer software product according to claim 13 into a data memory means of a computer and executing computer software instructions according to claim 13, which simulate operation of the laser materials processing and measurement device.

16. A method for operating a laser materials processing and measurement device with a controllable laser for generating a laser beam and beam control means for adjusting the focus zone of a controlled portion of the laser beam in three spatial directions, in particular in biological tissue, the method comprising:

providing an apparatus according to claim 1 and simulating operation of the laser materials processing and measurement device by simulating one or more of the following functions of the laser materials processing and measurement device:

basic settings of the laser materials processing and measurement device, predetermined types of calibration for the laser materials processing and measurement device, predetermined beam control tests for the beam control means of the laser materials processing and measurement device, predetermined surgical operations performed by the laser materials processing and measurement device, predetermined beam deflection functions performed by the beam control means, predetermined service functions of the laser materials processing and measurement device, error codes of the laser materials processing and measurement device, predetermined limit values for operating parameters of the laser materials processing and measurement device, predetermined system operating parameters with regard to operation of the laser materials processing and measurement device, and predetermined system status parameters of the laser materials processing and measurement device.

17. A method according to claim 16, wherein the one or more functions of the laser materials processing and measurement device can be simulated even when the laser materials processing and measurement device is not operationally ready or not connected to the interface.

* * * * *